United States Patent
Jerussi

(12) 
(10) Patent No.: US 6,294,582 B1
(45) Date of Patent: Sep. 25, 2001

(54) METHODS FOR TREATMENT OF ASTHMA USING S-OXYBUTYNIN

(75) Inventor: Thomas P. Jerussi, Framingham, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/574,106

(22) Filed: May 17, 2000

Related U.S. Application Data

(60) Provisional application No. 60/135,069, filed on May 20, 1999.

(51) Int. Cl.$^7$ ............................ A61K 31/165; A61K 9/70
(52) U.S. Cl. ...................... 514/617; 514/534; 514/540; 514/826; 424/449
(58) Field of Search ................................ 514/617, 534, 514/540, 826; 424/449

(56) References Cited

U.S. PATENT DOCUMENTS

| | | | |
|---|---|---|---|
| 5,171,744 | * 12/1992 | Cross et al. | 514/305 |
| 5,532,278 | 7/1996 | Aberg | 514/617 |
| 5,677,346 | 10/1997 | Aberg | 51/617 |
| 5,736,577 | 4/1998 | Aberg | 514/612 |

FOREIGN PATENT DOCUMENTS

| | | |
|---|---|---|
| 42 10 659 A1 | 12/1993 | (DE) . |
| WO 95/09007 | 4/1995 | (WO) . |
| WO 96/23492 | 8/1996 | (WO) . |
| WO 98/00126 | 1/1998 | (WO) . |
| WO 98/01125 | 1/1998 | (WO) . |

OTHER PUBLICATIONS

Howell et al., "Pulmonary Pharmacology of a Novel, Smooth Muscle–Selective Muscarinic Antagonist In Vivo", The Journal of Pharmacology and Experimental Therapeutics, 1994, Vo. 270, No. 2, pp. 546–553.

Characterization of the airway smooth muscle muscarinic receptor in vivo, Howell et al., European Journal of Pharmacology, 197 (1991) 109–112.

* cited by examiner

*Primary Examiner*—Frederick Krass
(74) *Attorney, Agent, or Firm*—Heslin Rothenberg Farley & Mesiti P.C.

(57) ABSTRACT

Substantially optically pure S-oxybutynin, or a pharmaceutically acceptable salt thereof, is administered as a treatment for asthma. Such treatment is provided while reducing the adverse effects associated with the administration of racemic oxybutynin.

16 Claims, No Drawings

METHODS FOR TREATMENT OF ASTHMA USING S-OXYBUTYNIN

TECHNICAL FIELD

This application claims the benefit of Provisional Application No. 60/135,069, filed May 20, 1999.

The present invention relates to methods for treatment of asthma using S-oxybutynin.

BACKGROUND OF THE INVENTION

Asthma, bronchitis and emphysema are known as Chronic Obstructive Pulmonary Diseases (COPD). COPD is characterized as generalized airways obstruction, particularly of small airways, associated with varying degrees of symptoms of chronic bronchitis, asthma, and emphysema. The term COPD was introduced because these conditions often coexist, and it may be difficult in an individual case to decide which is the major condition producing the obstruction. Airways obstruction is defined as an increased resistance to airflow during forced expiration. It may result from narrowing or obliteration of airways secondary to intrinsic airways disease, from excessive collapse of airways during a forced expiration secondary to pulmonary emphysema, from bronchospasm as in asthma, or may be due to a combination of these factors. Although obstruction of large airways may occur in all these disorders, particularly in asthma, patients with severe COPD characteristically have major abnormalities in their small airways, namely those less than 2 mm internal diameter, and much of their airways obstruction is situated in this zone. The airways obstruction is irreversible except for that which can be ascribed to asthma.

Asthma is a reversible obstructive pulmonary disorder (ROPD) characterized by increased responsiveness of the airway, resulting in airway obstruction. Airway obstruction is defined as an increased resistance to air flow during forced expiration. In asthma, airway obstruction typically results from bronchospasm. The underlying mechanisms causing asthma are unknown, but inherited or acquired imbalance of adrenergic and cholinergic control of airway diameter has been implicated. Asthmatics manifesting such imbalance have hyperactive bronchi and, even without symptoms, bronchoconstriction may be present. Overt asthma attacks may occur when such individuals are subjected to various stresses, such as viral respiratory infection, exercise, emotional upset, nonspecific factors (e.g., changes in barometric pressure or temperature), inhalation of cold air or irritants (e.g., gasoline fumes, fresh paint and noxious odors, or cigarette smoke), exposure to specific allergens, and ingestion of aspirin or sulfites in sensitive individuals. Those whose asthma is precipitated by allergens (most commonly airborne pollens and molds, house dust, animal danders) and whose symptoms are IgE-mediated are said to have allergic or "extrinsic" asthma. They account for about 10 to 20% of adult asthmatics; in another 30 to 50%, symptomatic episodes seem to be triggered by non-allergenic factors (e.g., infection, irritants, emotional factors), and these patients are said to have non-allergic or "intrinsic" asthma. In many persons, both allergenic and non-allergenic factors are significant.

Oxybutynin is used therapeutically in the treatment of intestinal hypermotility and in the treatment of urinary incontinence due to detrusor instability. Oxybutynin is sold for this purpose under the trade name of Ditropan®. Chemical names for oxybutynin are 4-(diethylamino)-2-butynyl-α-cyclohexyl-α-hydroxy benzeneacetate, and 4-(diethylamino)-2-butynylphenylcyclohexyl-glycolate. It is a racemic mixture of the R-enantiomer, R-oxybutynin, and the S-enantiomer, S-oxybutynin.

Use of the S-enantiomer of oxybutynin, S-oxybutynin, for the treatment of urinary incontinence has been described in U.S. Pat. No. 5,532,278, and 5,736,577. The structure of S-oxybutynin (Registry Number 119618-22-3) is shown in formula I. S-oxybutynin is not commercially available at the present time.

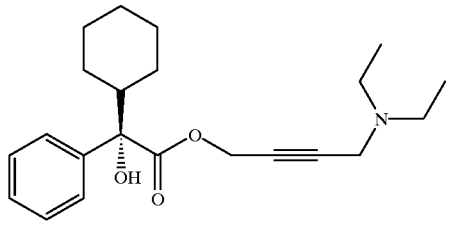

Administration of racemic oxybutynin may result in a number of adverse effects. These adverse effects include, but are not limited to, xerostomia, mydriasis, drowsiness, nausea, constipation, palpitations and tachycardia. The amelioration of cardiovascular side effects of racemic oxybutynin, such as tachycardia and palpitations, is of particular therapeutic value.

There is a continuing need for treatments for asthma, particularly those that minimize side effects.

SUMMARY OF INVENTION

It has now been found unexpectedly that S-oxybutynin provides a superior therapy for the treatment of reversible obstructive pulmonary disorders, including asthma, and provides this treatment while substantially reducing the adverse effects that are associated with the administration of racemic oxybutynin for other indications.

In one aspect, the present invention relates to a method of treating ROPD comprising administering to an individual in need of such therapy a therapeutically effective quantity of substantially optically pure S-oxybutynin, or a pharmaceutically acceptable salt thereof. In another aspect, such treatment is provided while reducing the adverse effects associated with the administration of racemic oxybutynin. Preferably, the treatment comprises inducing bronchodilation or relieving or preventing bronchoconstriction. The therapeutically effective quantity is preferably a quantity sufficient to reverse or prevent bronchospasms and the substantially optically pure S-oxybutynin preferably comprises at least 98% by weight of the S-isomer and 2% or less by weight of the R-isomer.

The S-oxybutynin may be administered orally, rectally, or by subcutaneous injection, intravenous infusion, inhalation or transdermal delivery. Preferably, the S-oxybutynin is administered orally, by inhalation or in the form of a transdermal patch. Where administration is by mouth, preferred forms are syrups, tablets or capsules. The amount administered orally is preferably from about 1 mg to about 1 g per day, more preferably from about 25 mg to about 700 mg per day. The amount administered by inhalation is preferably from about 0.1 mg to about 100 mg per day.

DETAILED DESCRIPTION

The present invention encompasses a method of treating reversible obstructive pulmonary diseases (ROPD), including asthma while reducing the adverse effects associated with administration of racemic oxybytynin which comprises administering to an individual in need of such therapy, a therapeutically effective quantity of substantially optically pure S-oxybutynin, or a pharmaceutically acceptable salt thereof. The quantity administered is preferably sufficient to reverse or prevent bronchospasms. Preferred methods of treating ROPD are inducing bronchodilation and relieving or preventing bronchoconstriction, as these provide relief from the symptoms associated with ROPD which include but are not limited to respiratory distress, wheezing, coughing, shortness of breath, and tightness or pressure in the chest.

The term "substantially optically pure" as used herein means that the oxybutynin used contains at least about 90% by weight of the stereo isomer of oxybutynin specified, that is the S-isomer and 10% or less by weight of the R-isomer. In a preferred embodiment the oxybutynin used contains at least 98% by weight of the S-stereoisomer of oxybytynin and 2% or less of the R-stereoisomer.

The synthesis of S-oxybutynin has been described in the literature by Kacher et al., *J. Pharmacol. Exp. Ther.*, 247, 867–872 (1988). An improved synthetic method is disclosed in copending U.S. patent application, Ser. No. 09/211,646, now U.S. Pat. No. 6,140,529, the contents of which are incorporated in their entirety. In this method, an activated derivative of cyclohexylphenylglycolic acid (CHPGA), the mixed anhydride I, is prepared.

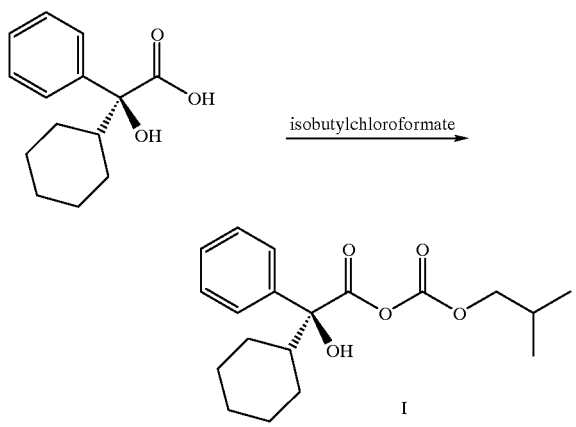

The mixed anhydride I is coupled with the propargyl alcohol derivative 4-N,N-diethylamino butynol (4-N,N-DEB)(III where $R^1$ is —$CH_2R^2$; $R^2$ is —$NR^3R^4$; and $R^3$ and $R^4$ are each ethyl.) Reaction of the optically active mixed anhydride with 4-N,N-DEB produces a single enantiomer of oxybutynin, in this case, (S)-4-diethylamino-2-butynylphenylcyclohexylglycolate.

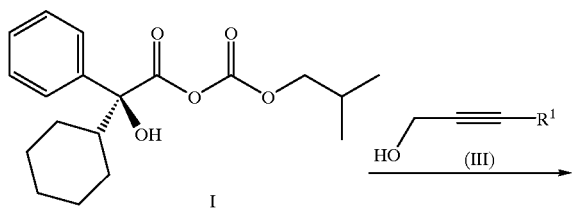

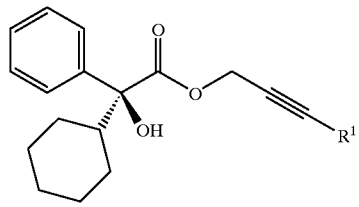

Improved syntheses of starting material CHPGA have been described in two copending U.S. patent applications, Ser. No. 09/050,825, now U.S. Pat. No. 6,013,830, and 09/050,832. The contents of both are incorporated by reference in their entirety. In the first (09/050,825, now U.S. Pat. No. 6,013,830), phenylglyoxylic acid or cyclohexylglyoxylic acid is condensed with a single enantiomer of a cyclic vicinal aminoalcohol to form an ester of the phenylglyoxylic acid or the cyclohexylglyoxylic acid. The ester is reacted with an appropriate Grignard reagent to provide an a-cyclohexylphenylglycolate ester. A single diastereomer of the product ester is separated from the reaction mixture, and hydrolyzed to provide S-α-cyclohexylphenylglycolic acid (S-CHPGA). The second (09/050,832) discloses an alternate stereoselective process for preparing CHPGA. A substituted acetaldehyde is condensed with mandelic acid to provide a 5-phenyl-1,3-dioxolan-4-one, which is subsequently reacted with cyclohexanone to provide a 5-(1-hydroxy cyclohexyl)-5-phenyl-1,3-dioxolan-4-one. The product is dehydrated to a 5-(1-cyclohexenyl)-5-phenyl-1,3-dioxolan-4-one, hydrolyzed and reduced to CHPGA.

The magnitude of a prophylactic or therapeutic dose of S-oxybutynin in the acute or chronic management of disease will vary with the severity of the condition to be treated, and the route of administration. The dose, and perhaps the dose frequency will also vary according to the age, body weight, and the response of the individual patient. In general, the daily dose ranges when administered by inhalation, for the conditions described herein, are from about 0.1 mg to about 100 mg in single or divided dosages. Preferably a daily dose range should be between about 10 mg to about 25 mg, in single or divided dosages, preferably in from 2–4 divided dosages. In managing the patient the therapy should be initiated at a lower dose, perhaps from 5 mg to about 10 mg, and increased up to about 2×20 mg or higher depending on the patient's global response. When administered orally, preferably as a soft elastic gelatin capsule, the preferred dose range is from about 1 mg to about 1 g per day, more preferably, from about 25 mg to about 700 mg per day, and most preferably, from about 100 mg to about 400 mg per day. It is further recommended that children and patients over 65 years and those with apaired renal, or hepatic function, initially receive low dosages and that they be titrated based on individual responses and blood levels. It may be necessary to use dosages outside these ranges in some cases, as will be apparent to those skilled in the art. Further, it is noted that the clinician or treating physician possesses knowledge of how and when to interrupt, adjust, or terminate therapy in conjunction with individual patient response. The terms "a therapeutically effective quantity", and "a quantity sufficient to alleviate bronchospasms" are encompassed by the above described dosage amounts and dose frequency schedule.

The methods of the present invention utilize S-oxybutynin, or a pharmaceutically acceptable salt thereof. The term "pharmaceutically acceptable salt" or "a pharmaceutically acceptable salt thereof" refer to salts prepared from pharmaceutically acceptable nontoxic acids including both inorganic and organic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluene sulfonic. The hydrochloride has particular utility.

Preferred unit dosage formulations are those containing an effective dose, as recited, or an appropriate fraction thereof, of S-oxybutynin or pharmaceutically acceptable salts thereof. The formulations of this invention may include other agents conventional in the art having regard to the type of formulation in question. For example, formulations for oral administration may include carriers such as starches, sugars, microcrystalline cellulose, diluents, granulating agents, flavoring agents and the like. Formulations suitable for oral, rectal and parenteral administration (including subcutaneous, transdermal, intramuscular, and intravenous) and inhalation may be used for treatment according to the present invention.

Any suitable route of administration may be employed for providing the patient with an effective dosage of S-oxybutynin. For example, oral, rectal, parenteral (subcutaneous, intramuscular, intravenous), transdermal, and like forms of administration may be employed. Transdermal administration may be improved by the inclusion of a permeation enhancer in the transdermal delivery device, for example as described in PCT application WO 92/20377. Dosage forms include troches, dispersions, suspensions, solutions, aerosols, patches, syrups, tablets and capsules, including soft elastic gelatin capsules. Oral and parenteral sustained release dosage forms may also be used.

Because of their ease of administration, tablets and capsules represent one of the more advantageous oral dosage unit forms, in which case solid pharmaceutical carriers are employed. If desired, tablets may be coated by standard aqueous or nonaqueous techniques. Soft elastic gel capsules are a preferred form of administration of S-oxybutynin.

Soft elastic gelatin capsules may be prepared by mixing S-oxybutynin with a digestible oil such as soybean oil, lecithin, cottonseed oil, or olive oil. The mixture is then injected into gelatin by means of a positive pressure pump, such that each dosage unit contains an effective dose of S-oxybutynin. The capsules are subsequently washed and dried.

Oral syrups, as well as other oral liquid formulations, are well known to those skilled in the art, and general methods for preparing them are found in most standard pharmacy school textbooks. An exemplary source is *Remington: The Science and Practice of Pharmacy*. Chapter 86 of the 19th edition of Remington entitled "Solutions, Emulsions, Suspensions and Extracts" describes in complete detail the preparation of syrups (pages 1503–1505) and other oral liquids. Similarly, sustained release formulation is well known in the art, and Chapter 94 of the same reference, entitled "Sustained-Release Drug Delivery Systems", describes the more common types of oral and parenteral sustained-release dosage forms (pages 1660–1675.) The relevant disclosure, Chapters 86 and 94, is incorporated herein by reference.

Controlled release means and delivery devices are also described in U.S. Pat. Nos. 3,845,770; 3,916,899; 3,536,809; 3,598,123; and 4,008,719, and in PCT application WO 92/20377. Because they reduce peak plasma concentrations, controlled release dosage forms are particularly useful for providing a therapeutic plasma concentration of S-oxybutynin while avoiding the side effects associated with peak plasma concentrations.

Formulations suitable for inhalation include sterile solutions for nebulization comprising a therapeutically effective amount of S-oxybutynin or a pharmaceutically acceptable salt thereof, dissolved in aqueous saline solution and optionally containing a preservative such as benzalkonium chloride or chlorobutanol, and aerosol formulations comprising a therapeutically effective amount of S-oxybutynin, or a pharmaceutically acceptable salt thereof, dissolved or suspended in an appropriate propellant (e.g., HFA-134a, HFA-227, or a mixture thereof, or a chlorofluorocarbon propellant such as a mixture of Propellants 11, 12 and/or 114) optionally containing a surfactant. Aerosols may be conveniently presented in unit dosage form and prepared by any of the methods well-known in the art of pharmacy. The preparation of a particularly desirable aerosol formulation is described in European Patent No. 556239, the disclosure of which is incorporated herein by reference. Also suitable are dry powder formulations comprising a therapeutically effective amount of S-oxybutynin or a pharmaceutically acceptable salt thereof, blended with an appropriate carrier and adapted for use in connection with a dry-powder inhaler.

| Example 1 - Inhalation Formulation | |
|---|---|
| Ingredient | Quantity Contained in Each Metered Dose Dispenser |
| S-oxybutynin hydrochloride | 1.8 g |
| trichloromonofluoromethane | 5.16 g |
| dichlorodifluoromethane | 5.16 g |
| sorbitan trioleate | 0.105 g |

The metered dose dispenser contains micronized S-oxybutynin hydrochloride in suspension. Each actuation delivers 10 mg of S-oxybutynin hydrochloride from the mouthpiece. Each canister provides about 200 inhalations.

| Example 2 - Oral Formulation | | |
|---|---|---|
| | Quantity | |
| Ingredient | Per Tablet (mg) | Per 10,000 Tablets (g) |
| S-oxybutynin hydrochloride | 10 | 100 |
| Lactose (granular, 12-mesh) | 35 | 350 |
| Cornstarch | 25 | 250 |
| Talc | 25 | 250 |
| Magnesium Stearate | 0.2 | 2 |
| Total | 150.0 | 59.0 |

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

What is claimed is:

1. A method of treating reversible obstructive pulmonary disease comprising administering to an individual in need of such therapy a therapeutically effective quantity of substantially optically pure S-oxybutynin, or a pharmaceutically acceptable salt thereof.

2. A method of treating reversible obstructive pulmonary disease while reducing the adverse effects associated with the administration of racemic oxybutynin comprising administering a therapeutically effective quantity of substantially optically pure S-oxybutynin, or a pharmaceutically acceptable salt thereof, to an individual in need of such therapy.

3. The method of claim 1, wherein treating reversible obstructive pulmonary disease comprises inducing bronchodilation.

4. The method of claim 1, wherein treating reversible obstructive pulmonary disease comprises relieving or preventing bronchoconstriction.

5. The method of claim 1, wherein the therapeutically effective quantity is a quantity sufficient to reverse or prevent bronchospasms.

6. The method of claim 1, wherein the substantially optically pure S-oxybutynin comprises at least 98% by weight of the S-isomer and 2% or less by weight of the R-isomer.

7. The method of claim 1, wherein S-oxybutynin is administered orally, rectally, or by subcutaneous injection, intravenous infusion, inhalation or transdermal delivery.

8. The method of claim 7, wherein S-oxybutynin is administered orally.

9. The method of claim 8, wherein S-oxybutynin is administered in the form of a syrup.

10. The method of claim 8, wherein S-oxybutynin is administered in the form of a tablet or a capsule.

11. The method of claim 10, wherein S-oxybutynin is administered in sustained release form.

12. The method of claim 8, wherein the amount administered orally is from about 1 mg to about 1 g per day.

13. The method of claim 8, wherein the amount of S-oxybutynin, or a pharmaceutically acceptable salt thereof, administered is from about 25 mg to about 700 mg per day.

14. The method of claim 7, wherein S-oxybutynin is administered by inhalation.

15. The method of claim 14, wherein the amount administered by inhalation is from about 0.1 mg to about 100 mg per day.

16. The method of claim 7, wherein S-oxybutynin is administered in the form of a transdermal patch.

* * * * *